United States Patent [19]

Ross

[11] Patent Number: 5,089,015
[45] Date of Patent: Feb. 18, 1992

[54] METHOD FOR IMPLANTING UNSTENTED XENOGRAFTS AND ALLOGRAFTS

[75] Inventor: Donald N. Ross, London, England

[73] Assignee: Promedica International, Newport Beach, Calif.

[21] Appl. No.: 442,951

[22] Filed: Nov. 28, 1989

[51] Int. Cl.$^5$ .............................................. A61F 2/00
[52] U.S. Cl. ..................................................... 623/2
[58] Field of Search ............... 606/144, 148, 1; 623/2, 623/900

[56] References Cited

U.S. PATENT DOCUMENTS

| | | | |
|---|---|---|---|
| 3,409,013 | 11/1968 | Berry | 606/1 |
| 3,546,710 | 12/1970 | Shumakov et al. | 623/2 |
| 3,628,535 | 12/1971 | Ostrowsky et al. | 623/2 |
| 3,710,744 | 1/1973 | Goodenough et al. | |
| 3,828,787 | 8/1974 | Anderson et al. | |
| 3,860,005 | 1/1975 | Anderson et al. | |
| 4,078,268 | 3/1978 | Possis | 623/2 |
| 4,182,446 | 1/1980 | Penny | |
| 4,185,636 | 1/1980 | Gabbay et al. | 606/148 |
| 4,211,325 | 7/1980 | Wright | |
| 4,506,394 | 3/1985 | Bedard | 623/2 |
| 4,585,453 | 4/1986 | Martin et al. | 623/2 |
| 4,655,218 | 4/1987 | Kulik et al. | |
| 4,679,556 | 7/1987 | Lubock et al. | |
| 4,683,883 | 8/1987 | Martin | |
| 4,702,250 | 10/1987 | Ovil et al. | 606/148 |
| 4,736,749 | 4/1988 | Lundback | |
| 4,801,015 | 1/1989 | Lubock et al. | |
| 4,834,097 | 5/1989 | Phillips et al. | |
| 4,865,600 | 9/1989 | Carpentier et al. | 623/900 |

FOREIGN PATENT DOCUMENTS 2108393A 5/1983 United Kingdom .

Primary Examiner—Max Hindenburg
Assistant Examiner—Gary Jackson
Attorney, Agent, or Firm—Lyon & Lyon

[57] ABSTRACT

A holder for providing physiologic support to an unstented xenograft or allograft. The holder facilitates selection and implantation of a replacement unstented xenograft or allograft in the treatment of aortic heart valve dysfunction. The novel holder comprises a device replicating key dimensions of the recipient native aortic root and incorporates a trimming guide. The holder is designed for several common sizes of the recipient native aortic root and annulus.

1 Claim, 6 Drawing Sheets

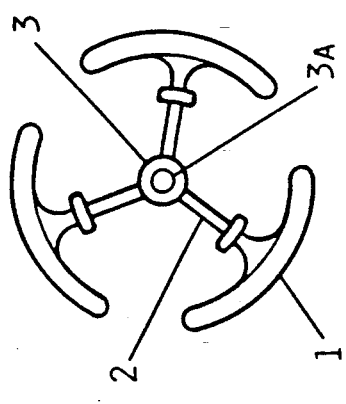
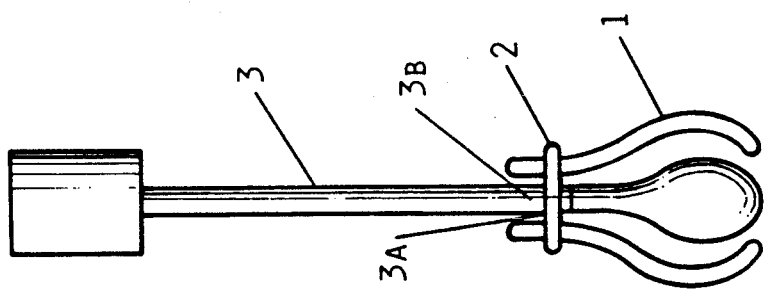

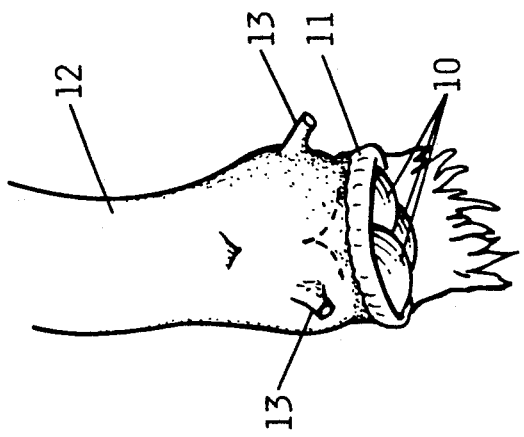
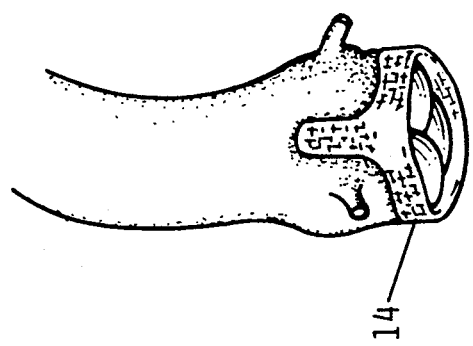
HOMOGRAFT
FIGURE 3A.  FIGURE 3B.
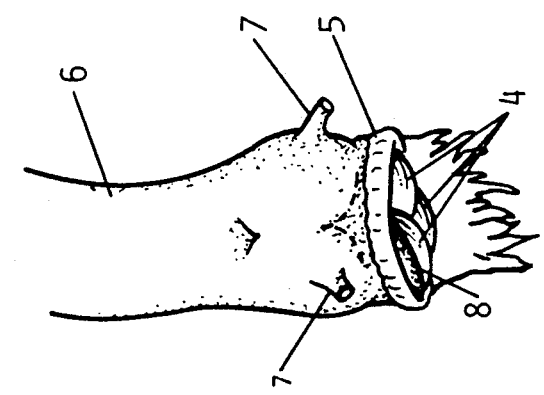
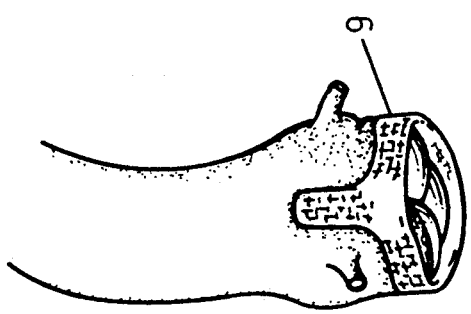
PORCINE
FIGURE 2A.  FIGURE 2B.

PORCINE

HOMOGRAFT

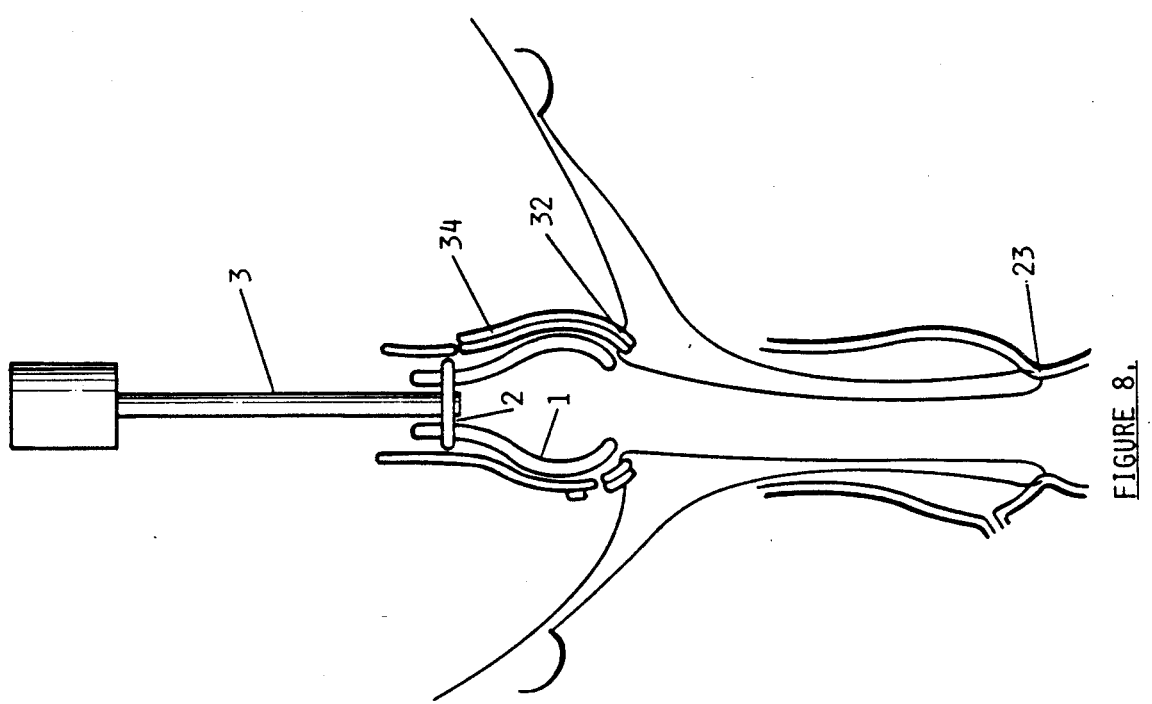

METHOD FOR IMPLANTING UNSTENTED XENOGRAFTS AND ALLOGRAFTS

FIELD OF THE INVENTION

This invention relates to the field of medicine, and in particular to a method of treating heart valve dysfunction in a human patient by replacing an existing valve with an unstented or freehand porcine aortic valve, porcine pulmonary valve, aortic allograft or pulmonary allograft.

TECHNOLOGY REVIEW

The human heart includes two valved chambers (left and right ventricles) for pumping blood through the body. Each ventricle has two valves to control flow of the blood into and out of it. In the case of the right ventricle they are the tricuspid and pulmonary valves and in the case of the left ventricle they are the mitral and aortic valves. During each cycle of the heart's operation, the mitral and tricuspid valves are simultaneously open allowing blood to flow into the ventricles while the aortic and pulmonary valves are closed. The ventricles then contract, and the resulting blood pressure therein closes the mitral and tricuspid valves while opening, and forcing blood outward through and opening the aortic and pulmonary valves.

In some individuals one or more valves may not function normally, usually as a result of disease-induced valve damage, degeneration or a congenital defect. In the case of the aortic valve, in particular, dysfunction often results from a narrowing of the valve orifice (stenosis), or from valve regurgitation such that the valve does not fully open or close. Severe valve dysfunction is life threatening. For the past 25 years, severe valve dysfunction has been treated by replacing the valve with a mechanical prosthesis, or alternatively, with a tissue valve (i.e., a valve of human or animal tissue). Tissue valves have the advantage of a lower incidence of blood clotting (thrombosis). Hence patients receiving such a valve, Unlike those receiving a mechanical valve, do not usually require prolonged anticoagulation therapy with its potential complications and patient inconvenience.

In the case of human aortic valve replacement, a commonly used tissue valve can be categorized as an allograft (usually an aortic valve from a cadaver, sometimes referred to as a homograft). In addition, some human aortic valves have been replaced with pulmonary autografts, that is a pulmonary valve from the same patient which in turn is then replaced with an allograft or a tissue valve constructed from nonvalvular tissue (eg. pericardium). The use of pulmonary autografts to replace a patient's aortic valve, is first described by Ross, *Lancet*, 1967, Vol. 2, 956; and also later described by Matsuki et al., *J. Thorac and Cardiovas. Surg.*, Vol. 95, p. 705 (1988); and "Tissue Heart Valves", ed. M. I. Ionescu, publisher Butterworth Inc., Boston, Mass., U.S.A. (1979) particularly at pp. 146-172. The foregoing references and all other references cited herein, are incorporated by reference.

Xenografts (a heart valve from another animal) are also commonly used for human valve replacement. In particular, the porcine aortic valve is often used since it is similar in anatomy to the human aortic valve (both being trileaflet) and is readily available in a variety of sizes. The porcine aortic xenograft has been used for human valve replacement, both stented (i.e. mounted in a frame such as those described in "Tissue Heart Valves", supra., particularly at pp 32-34, 107-109, and 177), and unstented (ref).

Unstented valves require a more exacting surgical procedure for insertion into a patient than do stented valves, and correct valve selection, orientation, and sizing is important to avoid valve distortion and subsequent malfunction. Correct valve selection requires calibration of the annulus, the commissural dimensions and intercommissure spacing. The presently used technique of implanting an unstented xenograft or allograft requires holding the flaccid valve between the fingers and estimating the appropriate suture placement relative to the diseased aortic root. Such a technique complicates the insertion procedure and frequently results in geometric mismatch of the replacement valve with the recipient's native aortic root. Due to the foregoing difficulties, many surgeons currently prefer to implant stented valves even though unstented valves, both xenografts and allografts, minimize turbulence and should therefore reduce thrombosis and embolism in comparison to stented valves.

SUMMARY OF THE INVENTION

The present invention provides a novel implement, and technique of using the same, which facilitates accurate selection and surgical insertion of an unstented aortic or pulmonary xenograft or freehand aortic or pulmonary allograft for valve replacement. The implement of the present invention therefore provides a means of temporarily supporting the xenograft or allograft to facilitate its correct insertion. The present invention facilitates correct trimming of the aortic (or pulmonary) artery segment in preparation for suturing the commissures to the recipient's native aortic wall.

The implement of the present invention includes an elongated handle and a base. Additionally, support members are provided which extend in a first direction from the base. The support members have outwardly enlarged ends, and are preferably spoon shaped with outwardly convex ends, so that they can contact and support the sinuses of a heart valve. A receptacle on the base can releasably engage an end of the handle such that the handle extends in a direction opposite the support members. The implement is used to hold, and assist in positioning, an unstented allograft or xenograft prior to and during implantation into a patient.

DRAWINGS

Embodiments of the invention will now be described with reference to the drawings, in which:

FIG. 1a is a perspective view of a holder of the present invention;

FIG. 1b is the top view of the holder of FIG. 1a;

FIG. 2a is a perspective view of an unstented porcine aortic valve with an attached aortic artery segment. Notice the muscle bar on the right coronary cusp.

FIG. 2b is the same as FIG. 2a except showing the valve with a with dacron sleeve.

FIG. 3a is a perspective view of an unstented (freehand) allograft with an attached aortic artery segment. Notice the absence of a muscle bar.

FIG. 3b is the same as FIG. 3a except showing the valve with a dacron sleeve

FIG. 8 is a sectional view of an unstented valve supported by the holder of FIGS. 1a and 1b, as it is lowered into position inside the recipient native aortic root.

DETAILED DESCRIPTION OF EMBODIMENTS OF THE INVENTION

Figure 4A:
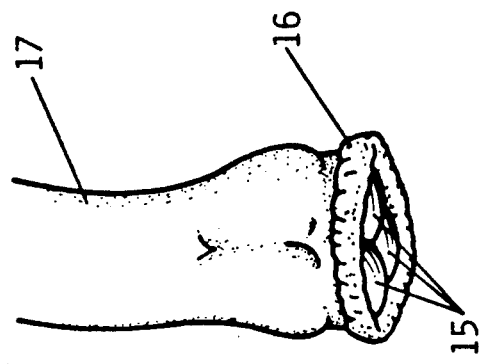
FIG. 4a is a perspective view of an unstented (freehand) porcine pulmonary valve with an attached pulmonary artery segment. Notice the absence of a muscle bar.
Figure 4B:
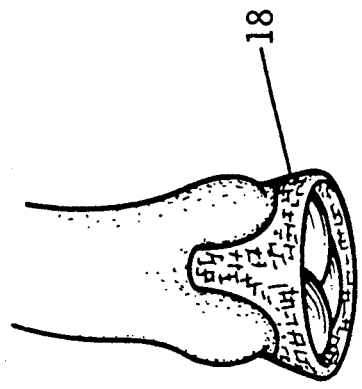
FIG. 4b is the same as FIG. 4a except showing the valve with a dacron sleeve.
Figure 5A:
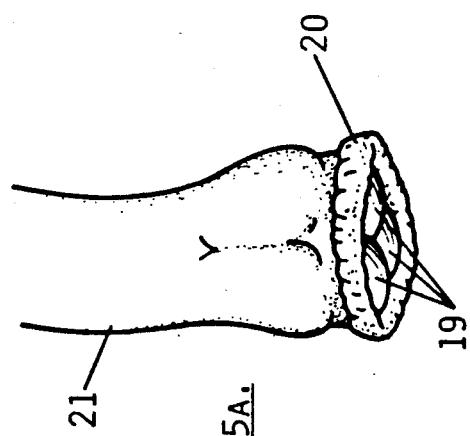
FIG. 5a is a perspective view of an unstented (freehand) allograft pulmonary valve with an attached pulmonary artery segment. Notice the absence of a muscle bar.
Figure 5B:
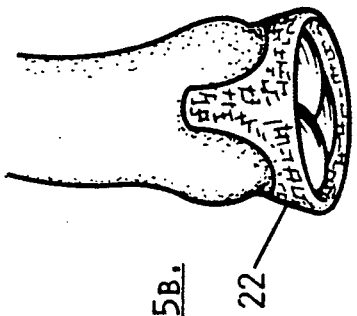
FIG. 5b is the same as FIG. 5a except showing the valve with a dacron sleeve.

Referring first to FIGS. 1a and 1b, the holder shown therein comprises a detachable handle 3, a triangular support 2 (sometimes referred to as a base), and three flexible spoon shaped sinus supports 1. A threaded female receptacle 3a is provided on support 2 to matingly receive a threaded end 3b of handle 3. The holder of FIGS. 1a and 1b can be used to support any of those valves shown in FIGS. 2a to 5b. FIG. 2a shows an unstented porcine aortic valve which essentially consists of three cusps 4, an aortic annulus 5 and an aortic artery segment 6, two coronary arteries 7 and a muscle bar 8 on the right coronary cusp. FIG. 2b shows the valve of FIG. 2a provided with a dacron sleeve 9 to facilitate suturing during implantation. FIG. 3a shows an unstented aortic allograft which essentially consists of three cusps 10, the aortic annulus 11, the aortic artery segment 12 and two coronary arteries 13. Note the absence of a muscle bar 8. FIG. 3b shows the valve of FIG. 3a provided with a dacron sewing sleeve 14. The unstented porcine pulmonary valve of FIG. 4a essentially consists of three cusps 15, the pulmonary valve annulus 16 and the pulmonary artery segment 17. Note the absence of a muscle bar 8. FIG. 4b shows the valve of FIG. 4a with a dacron sewing sleeve 18 provided. The unstented allograft pulmonary valve of FIG. 5a consists essentially of three cusps 19, the pulmonary annulus 20, and the pulmonary artery segment 21. Note the absence of a muscle bar 8. FIG. 5b shows the valve of FIG. 5a provided with a dacron sleeve 22.

Figure 6:
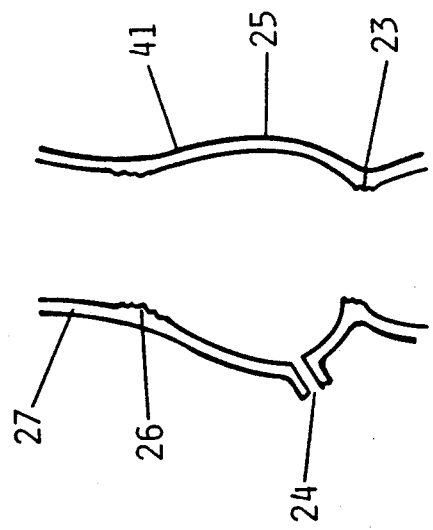
FIG. 6 is a sectional view of an aortic annulus and aorta of a patient, the native diseased valve having been excised.
Figure 11:
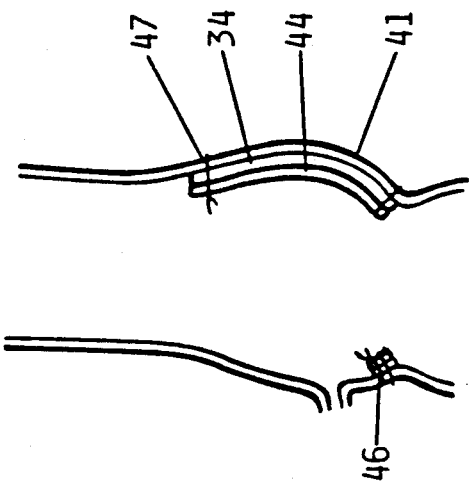
FIG. 11 is a sectional view of an unstented implanted valve inside the recipient native aortic root following trimming of the aortic (or pulmonary) artery segment.

Referring now to FIG. 6, there is shown a sectional view of a patient's recipient native aortic root 41, from which a diseased valve has previously been excised, ready to receive an implanted valve. At this point the native root consists of a raw annulus 23, two coronary arteries 24 (only one shown), three valve sinuses 25, three commissural remnants 26 and the aortic artery wall 27. A valve designated by numeral 34, and which may be of any of the foregoing described valve types, is implanted into the aortic root of FIG. 6 using the holder of FIGS. 1a and 1b, in the manner illustrated sequentially in FIGS. 7 to 11, and described below.

Figure 7:
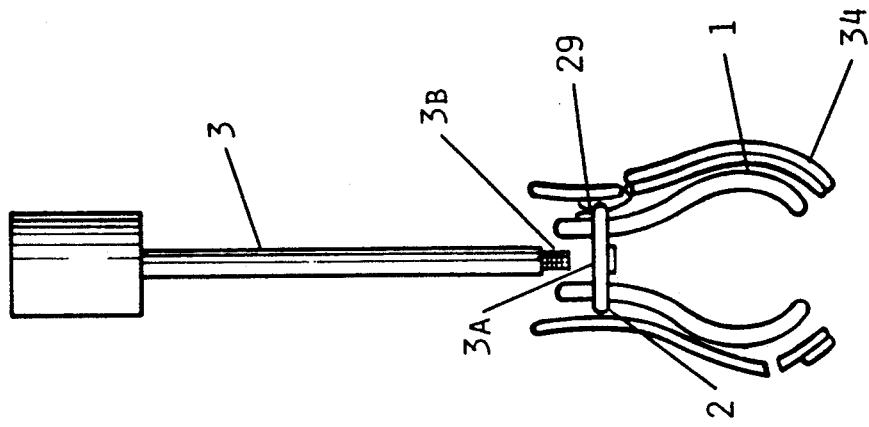
FIG. 7 is a sectional view of the holder of FIGS. 1a and 1b positioned in, and supporting, an unstented valve (with dacron covering) immediately prior to the attachment of the handle.
Figure 10:
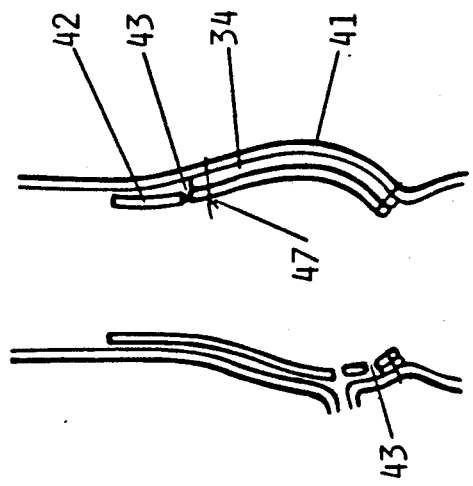
FIG. 10 is a sectional view of an unstented valve implanted inside the recipient native aortic root following removal of temporary stitches attached to the holder and consequent removal of the holder.
Figure 9:
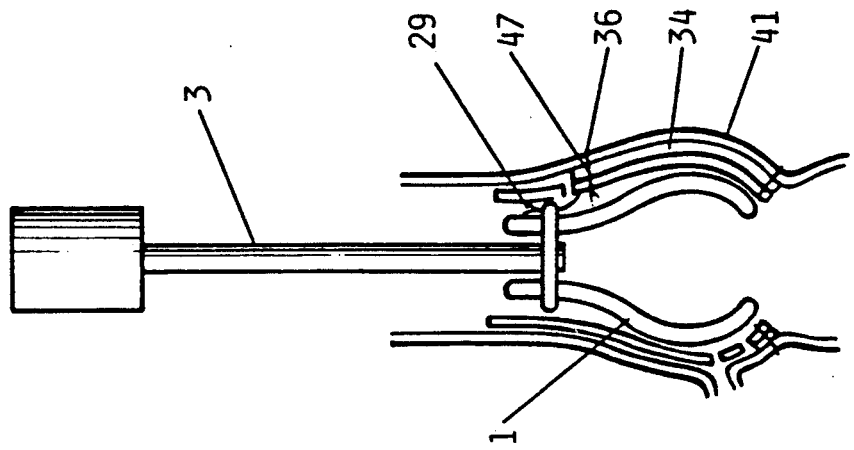
FIG. 9 is a sectional view of an unstented valve, supported by the holder of FIGS. 1a and 1b, positioned inside the recipient native aortic root following commissural suturing.

First, referring to FIG. 7, once the surgeon has excised the diseased aortic valve, the recipient native aortic root is sized, and an unstented porcine xenograft or allograft valve of the appropriate size is selected for implantation. The holder is temporarily secured by pilot sutures 29, inside the unstented valve. Handle 3 is then screwed into the screw fitting 3a of the holder. The unstented valve is then lowered into position inside the recipient native aortic root, to confirm the correct size and again withdrawn. Sutures are then placed through the unstented valve annulus 32 and then through the recipient native aortic annulus 23 in the manner illustrated in FIG. 8. Unstented valve 34 is lowered into place (as the sutures are tied) using handle 3. Referring now to FIG. 9, three permanent sutures 47 are placed at the top of each commissure 36. The temporary pilot sutures 29 are removed and the holder is removed using attached handle 3. At this point, the unstented valve 34 is left inside the recipient native aortic root 41, as shown in FIG. 10. An aortic (or pulmonary) artery segment 42 of the implanted valve is then removed by trimming along a trimming line 43 to produce trimmed unstented valve 44 inside the recipient native aortic root 41. Trimming line 43 is impressed onto the implanted valve as a result of appropriately shaped ridges (not shown) projecting outwardly from the holder and pressing into the implanted valve. Finally, a running continuous suture 46 is placed between the three commissural stitches 47 to completely secure the unstented valve 44 in position.

It will be appreciated that modifications to the embodiments described above, are of course possible. Accordingly, the present invention is not limited to the embodiments which have been described in detail above.

I claim:

1. A method of surgically implanting an unstented pulmonary or aortic valve into a human patient to replace the patient's aortic valve, using a holder having an elongated handle, a base, three generally spoon shaped support members extending in a first direction from the base to outwardly convex enlarged ends of the support members such that the support members can provide physiologic support for the valve sinuses, and a receptacle on the base which can releasably engage an end of the handle such that the handle extends in a direction opposite the support members, comprising:
   a) excising the patient's aortic valve while leaving the aortic root in place;
   b) inserting the support members of the holder into the unstented valve to be implanted, such that the support members provide physiologic support for the valve sinuses;
   c) releasably engaging an end of the handle in the base such that the handle extends outwardly through a pulmonary or aortic artery segment of the valve;
   d) inserting the supported valve temporarily into the patient's aortic root to confirm correct size;
   e) suturing the implanted valve in place in the patient's aortic root; and
   f) removing the holder by pulling on the handle.

* * * * *